(12) United States Patent
Jimenez-Rios

(10) Patent No.: US 9,518,898 B2
(45) Date of Patent: Dec. 13, 2016

(54) CRYOGENIC STORAGE CONTAINER WITH SEALING CLOSURE AND METHODS OF USING THE SAME

(71) Applicant: Cook Medical Technologies LLC, Bloomington, IN (US)

(72) Inventor: Jorge L. Jimenez-Rios, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 454 days.

(21) Appl. No.: 14/077,707

(22) Filed: Nov. 12, 2013

(65) Prior Publication Data

US 2014/0158695 A1    Jun. 12, 2014

Related U.S. Application Data

(60) Provisional application No. 61/734,057, filed on Dec. 6, 2012.

(51) Int. Cl.
| | |
|---|---|
| *F25B 19/00* | (2006.01) |
| *G01N 1/28* | (2006.01) |
| *A01N 1/02* | (2006.01) |
| *C12M 1/00* | (2006.01) |

(52) U.S. Cl.
CPC ............. *G01N 1/28* (2013.01); *A01N 1/0268* (2013.01); *C12M 45/22* (2013.01)

(58) Field of Classification Search
CPC .......... F25D 19/006; F25D 3/10; F17C 3/085; B01L 3/0275
USPC . 62/51.1, 62, 48.1, 371; 422/501; 220/560.4
See application file for complete search history.

(56) References Cited

U.S. PATENT DOCUMENTS

| | | |
|---|---|---|
| 129,094 A | 7/1872 | Briggs |
| 181,950 A | 9/1876 | Kromer |
| 308,217 A | 11/1884 | Truxall |
| 1,517,164 A | 11/1924 | Lear |
| 1,763,461 A | 6/1930 | Fowler |
| 2,315,425 A | 3/1943 | Hill et al. |
| 3,108,840 A | 10/1963 | Conrad et al. |
| 3,168,362 A | 2/1965 | Perkins |

(Continued)

FOREIGN PATENT DOCUMENTS

| | | |
|---|---|---|
| EP | 1774852 A2 | 4/2007 |
| FR | 2308068 | 4/1975 |

(Continued)

OTHER PUBLICATIONS

Patent Examination Report No. 1 for AU 2013355063 dated Jul. 23, 2015 (2 pages).

(Continued)

*Primary Examiner* — Melvin Jones
(74) *Attorney, Agent, or Firm* — Brinks Gilson & Lione

(57) ABSTRACT

A container or vial for the cryopreservation and/or vitrification and storage of a biological sample, including cellular samples and embryos is described. The container comprises a sealable closure that isolates a biological sample held in the container lumen from the external environment and is suitable for storage of the sample in liquid nitrogen. Methods for introducing and sealing biological samples within the container for cryopreservation and/or vitrification and storage are also described.

20 Claims, 2 Drawing Sheets

(56) References Cited

U.S. PATENT DOCUMENTS

| | | | |
|---|---|---|---|
| 3,419,179 A * | 12/1968 | Fritz Deuschle | B01L 3/5082 220/200 |
| 4,377,077 A | 3/1983 | Granlund | |
| 4,390,111 A | 6/1983 | Robbins et al. | |
| 4,509,587 A | 4/1985 | Clark et al. | |
| 4,755,356 A | 7/1988 | Robbins et al. | |
| 4,859,610 A | 8/1989 | Maggio | |
| 4,874,102 A | 10/1989 | Jessop et al. | |
| 5,325,980 A * | 7/1994 | Grimm | B01L 3/50825 215/213 |
| 5,382,409 A | 1/1995 | Baxter | |
| 5,711,446 A | 1/1998 | Jeffs et al. | |
| 5,850,917 A | 12/1998 | Denton et al. | |
| 5,894,733 A | 4/1999 | Brodner | |
| 5,916,525 A | 6/1999 | Husar et al. | |
| 6,047,845 A | 4/2000 | Rapaz | |
| 6,063,038 A | 5/2000 | Diamond et al. | |
| 6,065,294 A | 5/2000 | Hammerstedt et al. | |
| D427,691 S | 7/2000 | Asselta | |
| 6,701,743 B1 | 3/2004 | Durst et al. | |
| 6,805,842 B1 | 10/2004 | Bodner et al. | |
| 6,858,424 B2 | 2/2005 | Wisniewski | |
| 7,316,896 B2 | 1/2008 | Kuwayama et al. | |
| D630,478 S | 1/2011 | Bell | |
| 7,870,748 B2 | 1/2011 | Byrne | |
| 7,997,438 B2 | 8/2011 | Kelly | |
| 8,168,138 B2 | 5/2012 | Che et al. | |
| 8,177,123 B2 | 5/2012 | Voute et al. | |
| 8,640,899 B2 * | 2/2014 | Palusci | B65D 47/02 215/253 |
| 2005/0029914 A1 | 2/2005 | Wang | |
| 2006/0046243 A1 | 3/2006 | Stachecki et al. | |
| 2009/0120106 A1 | 5/2009 | Chin | |
| 2009/0123992 A1 | 5/2009 | Chin | |
| 2009/0123996 A1 | 5/2009 | Chin | |
| 2009/0186405 A1 | 7/2009 | Chin | |
| 2009/0255938 A1 | 10/2009 | Fuja | |
| 2011/0120148 A1 | 5/2011 | Yoshimura et al. | |
| 2011/0129811 A1 | 6/2011 | Tao | |
| 2011/0143452 A1 | 6/2011 | Che et al. | |
| 2011/0150706 A1 | 6/2011 | Murphy et al. | |
| 2011/0239791 A1 | 10/2011 | Fici | |
| 2011/0275153 A1 | 11/2011 | Butler et al. | |
| 2012/0061392 A1 | 3/2012 | Beach et al. | |

FOREIGN PATENT DOCUMENTS

| | | |
|---|---|---|
| FR | 2395780 | 1/1979 |
| GB | 2407314 | 4/2005 |
| JP | 2001 252293 | 9/2001 |
| WO | WO 83/02386 | 7/1983 |
| WO | WO 2010/008083 A1 | 1/2010 |
| WO | WO 2012/158963 A2 | 11/2012 |

OTHER PUBLICATIONS

Patent Examination Report No. 1 for Australian Patent App. No. 2013356415, dated Sep. 4, 2015, 3 pp.

Chemglass Life Sciences, CLS-4758, Cryovials, Extra Long Lip Seal, Internal Thread with Silicone Washer, CLS-4758, http://www.chemglass.com/product_view.asp?pnr=CLS-4758, retrieved on Oct. 1, 2015, 2 pp.

International Search Report and Written Opinion of the International Searching Authority for PCT/US2013/073539 dated Apr. 9, 2014 (10 pages).

"Cryovials & Accessories," (Chemglass Life Sciences) brochure, Feb. 1, 2010, XP055109581, Retrieved from the Internet: URL:http://chemglass.brookwood.com/pages/pdf/flyers/CryoVialBro_web.pdf [retrieved on Mar. 24, 2014] p. 2, 8 pages.

"Simport Micrewtubes | BioExpress Online," Nov. 26, 2012, Retrieved from the Internet: URL:http://web.archive.org/web/20121126034237/http://www.bioexpress.com/divinity-cart/item/464300/SIMPORT-Micrewtubes/1.html? [retrieved on Mar. 24, 2014], 3 pages.

H. Chen et al., "The derivation of two additional human embryonic stem cell lines from day 3 embryos with low morphological scores," Human Reproduction, vol. 20, No. 8, pp. 2201-2206, 2005.

PCT International Search Report and Written Opinion for corresponding PCT/US2013/071589, mailed Apr. 7, 2014, 12 pages.

International Preliminary Report on Patentability and Written Opinion for PCT/US2013/071589, dated Jun. 18, 2015, 8 pp.

* cited by examiner

CRYOGENIC STORAGE CONTAINER WITH SEALING CLOSURE AND METHODS OF USING THE SAME

RELATED APPLICATIONS

This application claims the benefit of priority of U.S. Provisional application Ser. No. 61/734,057 filed on Dec. 6, 2012, which application is incorporated by reference herein in its entirety.

TECHNICAL FIELD

The present invention relates generally to a container for cryopreservation and/or vitrification of a biological sample and more particularly, a cryocontainer with a sealing closure suitable for storage of a sample in liquid-phase nitrogen.

There are a variety of applications in which it is desirable to preserve and store biological samples, including tissue cultures and cells, in a controlled environment. Various containers and storage methods have been investigated in order to maximize the viability of a particular stored sample while minimizing cost, hazards and handling difficulties. One particular situation in which specific containers and storage techniques are carefully selected and performed arises in cryobanking and assisted reproduction clinics and facilities. For example, such facilities may commonly use cryocontainers for the cryopreservation and/or vitrification and storage of sperm, oocytes and embryos.

Extremely cold temperatures are commonly used for the preservation and storage of a particular biological sample. During conventional cryopreservation or "slow freeze", a biological specimen may be placed in a suitable cryocontainer and then chilled to a cryogenic storage temperature that is typically about −196 degrees C., the atmospheric boiling point of liquid nitrogen. An alternative to the above-mentioned cryopreservation method is vitrification. Typically, during vitrification, a very small cellular sample such as an embryo suspended in a vitrification preservation medium ("cryoprotectant") is rapidly cooled by direct immersion in, or alternatively, indirect exposure to, a cryogenic fluid or other freezing medium such as liquid nitrogen. The rapid cooling of the biological sample results in the sample becoming trapped in a glassy matrix (e.g. vitrified).

It is known to use liquid nitrogen vapors and/or liquid nitrogen or other suitable freezing media to achieve and maintain the extremely low temperature necessary to preserve the sample during cryopreservation and vitrification. However, the potential for the cross-contamination of biological samples stored in a cryocontainer in liquid nitrogen may sometimes exist. Accordingly, it is desirable to provide a simplified and improved cryocontainer compatible with and able to withstand the high cooling rates and temperature ranges required for cryopreservation and vitrification, including but not limited to, a container having a sealable closure that isolates a biological sample held therein from the external environment and that is suitable for storage in liquid nitrogen.

SUMMARY

The present disclosure provides a sealable container for the cryopreservation and/or vitrification and storage of a biological sample, including cellular samples and embryos. In one example, the sealable container comprises a body having a proximal open end and a sealed distal end and a variable diameter lumen extending there between. The lumen has an external surface and an internal surface, the internal surface tapering generally radially inwardly from the proximal open end to the distal end and forming a sealing portion and a sample receiving portion. The container further comprises a closure configured for removable attachment to the body. The closure preferably includes a capping member adapted for engagement with the proximal open end of the container and a deformable sealing member having a tapered external surface configured for sealing engagement with the sealing portion of lumen internal surface.

At least two projections extend radially outwardly from the external surface of the lumen which projections form a radially outward-most distal surface extending between the proximal open end and the sealed distal end of the body. The distal surface formed by the projections has a substantially constant diameter. An intermediate space may be located between the external surface of the lumen and the distal surface of the projections.

The present disclosure also provides a method for preparing a biological sample for cryogenic storage. In one example, the method comprises obtaining sealable container comprising a body having a proximal open end and a sealed distal end and a variable diameter lumen extending there between. The lumen preferably has an external surface and an internal surface, the internal surface tapering generally radially inwardly from the proximal open end to the distal end and forming a sealing portion and a sample receiving portion. The container used in the method also preferably comprises a closure configured for removable attachment to the body wherein the closure comprises a capping member adapted for engagement with the proximal open end and a deformable member having a tapered external surface configured for sealing engagement with the sealing portion of lumen internal surface. Preferably, at least two projections extend radially outwardly from the external surface of the lumen, the projections comprising a radially outward-most distal surface extending between the proximal open end and the sealed distal end of the body, wherein the distal surface has a substantially constant diameter. The method also further preferably includes introducing a biological sample into the lumen of the container and attaching the closure to the container body.

A cryogenic storage method is also provided. In one example, the method comprises introducing a biological sample into the lumen of a container. The container preferably comprises a body comprising a proximal open end and a sealed distal end and a variable diameter lumen extending there between, the lumen having an external surface and an internal surface, the internal surface tapering generally radially inwardly from the proximal open end to the distal end and forming a sealing portion and a sample receiving portion. The container also preferably comprises a closure configured for removable attachment to the body wherein the closure comprises a capping member adapted for engagement with the proximal open end and a deformable member having a tapered external surface configured for sealing engagement with the sealing portion of lumen internal surface. Preferably, at least two projections extend radially outwardly from the external surface of the lumen, the projections comprising a radially outward-most distal surface extending between the proximal open end and the sealed distal end of the body, wherein the distal surface has a substantially constant diameter. The method also preferably includes exposing at least a portion of the container to a cryogenic freezing medium. In one example of the method, the lumen of the container is pre-cooled to a temperature suitable for the vitrification of a biological sample prior to the step of introducing the biological sample into the lumen.

DETAILED DESCRIPTION

The examples and embodiments described below are primarily in connection with a sealable container suitable for the cryopreservation and vitrification of sperm cells, oocytes and/or embryos and storage thereof in liquid phase nitrogen, however, the described container may also be used in connection with a range of medical procedures and methods including the preservation and sealed storage of biological samples in a variety of environments and temperatures.

Figure 1:
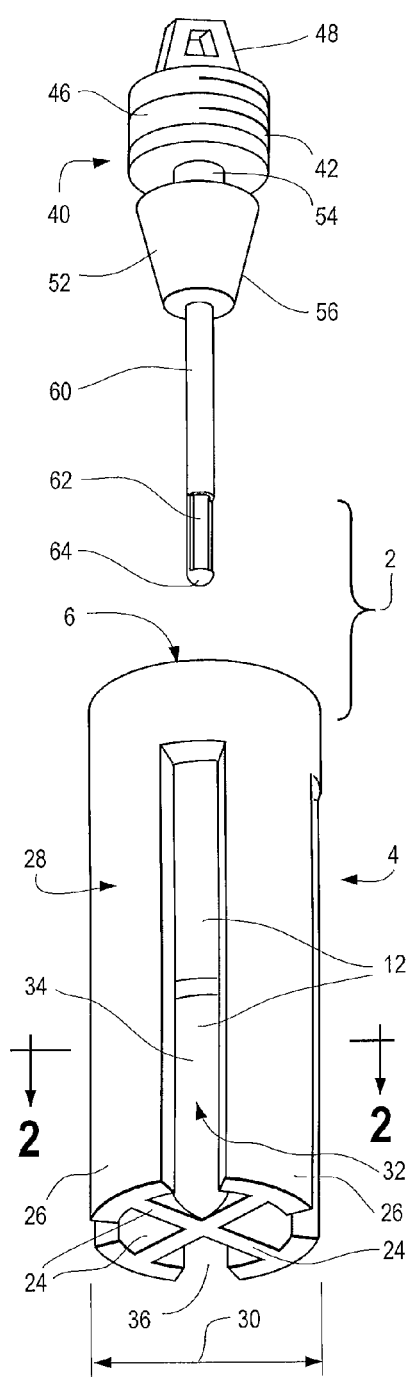
FIG. 1 is an expanded perspective view of one example of a cryocontainer and sealing closure.

FIG. 1 illustrates one example of a container adapted for receiving and storing a biological sample, identified generally at 2. The container 2 is preferably a vessel such as a tube or vial 4 suitable for use in the cryopreservation and/or vitrification and storage of biological samples. The terms "container", "vial", "cryocontainer" and "cryovial" may be used interchangeably to refer to a container that is suitable for conventional cryopreservation and also for vitrification unless otherwise noted, and for simplicity may simply be referred to herein as a "container". In one non-limiting example, the biological sample may include oocytes, a semen sample containing sperm cells and/or one or more embryos, but may also be applied to other cellular samples as will be apparent to those skilled in the art.

Figure 3:
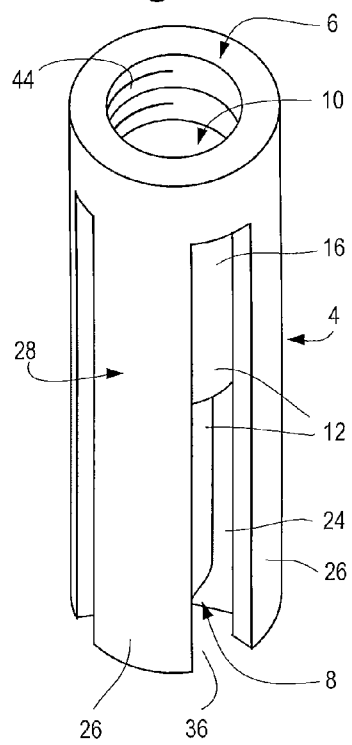
FIG. 3 is a perspective view of one example of a cryocontainer.
Figure 4:
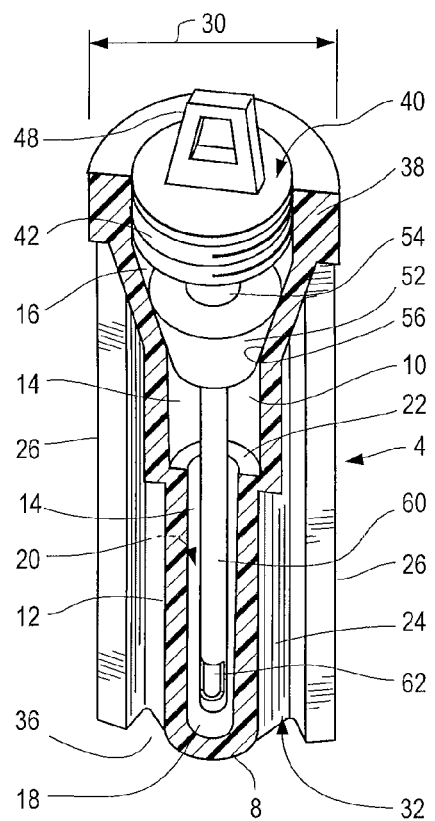
FIG. 4 is a side cross-sectional view of one example of a sealed cryocontainer with a stem for holding a biological sample to be vitrified extending from the sealable closure.
Figure 5:
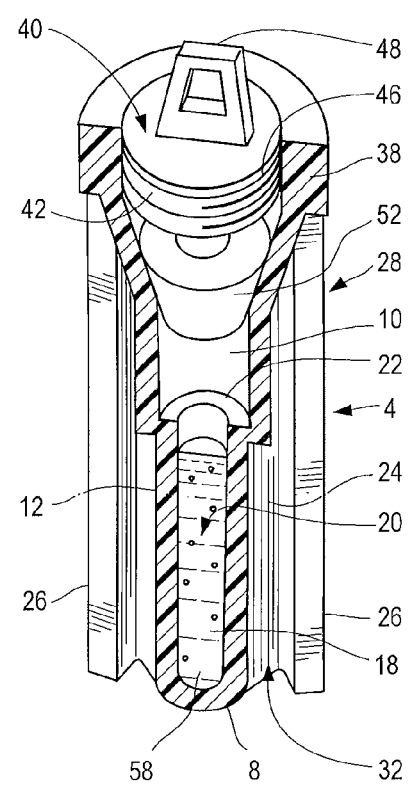
FIG. 5 is a side cross-sectional view of another example of a sealed cryocontainer containing a liquid biological sample or a suspension of cells in the distal end portion of the container lumen.

As shown in FIGS. 3, 4 and 5, the container 4 may include an open proximal end 6 and a sealed distal end 8, with a lumen 10 extending between the respective ends. The lumen has an internal surface 14 and an external surface 12. In one example, the internal surface 14 has a variable diameter, and preferably, the internal surface 14 of the lumen tapers radially inwardly from a wider 16 open proximal end 6 to a more narrow 18 sealed distal end 8, where a selected sample may be received 20 for cryopreservation or vitrification and held for storage. The taper may be gradual such that the lumen wall has a generally consistent taper angle between the proximal 6 and distal ends 8 or, alternatively, the taper may be stepped as FIGS. 4 and 5 illustrate, where the lumen 10 is wider 16 near the proximal end and one or more shoulders or annular ledges 22 leads to a relatively more narrow 18 sample receiving portion 20 near the sealed distal end 8 of the lumen 10. In one non-limiting example, the internal lumen 10 can vary in diameter from about 2 mm at the more narrow diameter portion to about 7 mm at the wider diameter portion.

Figure 2:
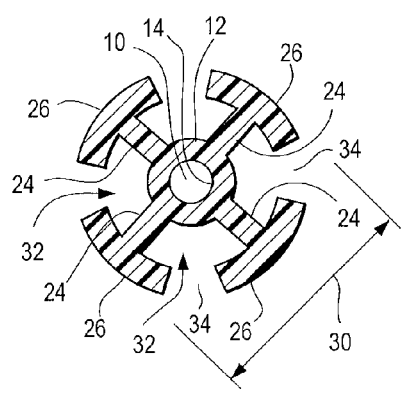
FIG. 2 is a cross-sectional view of one exemplary configuration of a cryocontainer with a series of projections extending radially outwardly from the container lumen.

As best illustrated in FIGS. 1 and 2, one or more protrusions or projections 24 extend radially outwardly from the external surface 12 of the container lumen 10. The projections 24 may be in the form of spokes, posts, wings, walls, panels, baffles or a combination thereof. The projections may be intermittently spaced or solid structures, and either integrally formed with the external surface 12 of the lumen wall or separately formed structures that are secured to the wall between the proximal 6 and distal 8 ends. Alternatively, the projections 24 may be in the form of one or more annular ring(s) or a tubular structure that encircles or substantially surrounds the external surface 12 of the lumen 10. As FIGS. 1 and 2 illustrate, the multiple projections 24 are preferably a series of generally T-shaped wings that extend from the external surface 12 of the lumen 10. The radially outward-most surface 26 of the protrusions (i.e. the top portion of the "T" shape in FIG. 2) preferably extends the longitudinal length of the container, thus forming an outer container surface generally at 28 having a relatively constant external diameter 30, although, it is also contemplated that the outward-most surface 26 of the protrusions 24 extend only partially along the length of the container between the proximal 6 and distal ends 8, and, like the lumen 10, may also have a variable diameter that is more narrow at one end and wider at the other end, for example. The outermost surface 26 of the protrusions 24 may have a diameter of approximately 12 mm, and preferably the shape and/or diameter of the protrusions 24 is configured to allow the container 4 to stand upright on a surface and/or be held snugly and securely in most standard sized commercially available tube holders, canes, racks, organizers and the like.

FIGS. 4 and 5 illustrate a side cross-sectional view of examples of a cryocontainer 4, and, as shown there, container 4 is preferably constructed of a single integral piece of material, such as by injection molding or the like, although, the container 4 may also be constructed of separately formed or molded pieces that are secured together by adhesive, bonding and the like. An intermediate space 32 is formed between the external surface 12 of the lumen 10 and a surface of the radially outwardly extending protrusions 24 such that air (or fluid in the event that the container is submerged in a liquid or gas) can flow into the intermediate space 32 and substantially surround the external lumen wall 12. Where the protrusions 24 are a series of T-shaped walls extending from the lumen external surface 12, air or fluid may enter the intermediate space 32 from both the sides and the bottom of the container by flowing through the spaces formed between the series of projections, including side slots 34 and bottom openings 36. Although both fluid and air can flow into the intermediate space 32 and surround the external wall 12 of the lumen 10, preferably nothing in the intermediate space can flow or otherwise enter the lumen 10, as the lumen wall is preferably non-permeable and is devoid of any openings.

As shown in FIGS. 4 and 5, near the open proximal end 6 of the container 4, the external surface 12 of the lumen 10 and a portion of the radially extending protrusions 24 merge or are otherwise securely bonded together to form a unitary thicker wall 38 near the proximal open end 6. The open end is preferably configured to receive and engage a closure member 40 therein, as described in further detail below.

For example, as shown in FIGS. 1, 4 and 5, the cryocontainer 4 includes a closure member 40 that may be removably received by the proximal open end 6 of the container. In one example, the closure member 40 comprises a proximal capping portion 42 that is configured to engage with the open end 6 of the container. Preferably, the open end of the container 6 and the capping portion 42 include corresponding inter-engaging structures that allow the closure 40 to be secured to the container open end. As FIG. 3 shows, the internal surface 14 of the lumen 10 includes a threaded portion 44, while the capping portion 42 of the closure 40 includes a corresponding threaded portion 46 such that the closure can be screwed into the open end 6 of the container and securely held in place therein. It is also contemplated that the open end of the container may include threads on an external surface of the unitary thicker wall 38 for engagement with the capping portion 42 which may be alternately configured for being fitted over the top of the container 4 rather than fitted within the lumen 10. Other corresponding engaging structures on the closure member 40 and on the container 4, respectively, may also be suitable for securing the closure to the container, such as structures configured for snap fit or interlocking engagement.

Turning back now to FIGS. 1, 4 and 5, the capping portion 42 includes a grip or handle 48, illustrated generally as a loop or tab, but which may be any protruding surface or member to allow the user to grasp the proximal most end of the closure 40, insert the closure into the open end 6 of the container, and secure the closure in place such as by twisting or screwing the closure until the threads 44, 46 (or other suitable engaging members) are tightly engaged.

The closure member 40 also preferably includes a sealing portion located just distal to the capping portion 42. As FIGS. 1, 4 and 5 illustrate, a deformable sealing member 52, such as a plug or stopper is provided. The sealing member 52 may be spaced from the capping portion 42 by a more narrow-diameter neck 54 or spacer, however, it is also contemplated that the capping portion 42 and sealing member 52 are integral with each other with no space, neck or openings there between. The sealing member 52 includes an external surface 56, which is preferably tapered radially inwardly, such that it corresponds to the shape and taper of the internal lumen wall 14. In one example, the sealing portion of the internal lumen comprises a tapered angle of between about 3% and 10%, and preferably about 6%. In other words, the lumen 10 comprises a female taper, while the deformable sealing member 52 provides a correspondingly shaped male taper which tightly and securely engage each other, such as by friction fit. In fact, the external tapered surface 56 of the sealing member 52 may have a diameter that is slightly larger than the portion of the internal lumen wall 14 that is intended to engage such that when the closure 40 is inserted into the lumen 10, the lumen internal surface 14 presses radially inwardly against the external surface 56 of the sealing member 52 to provide a leak-proof impermeable seal. Preferably, the seal created is impermeable to liquids and gasses, including liquid nitrogen, at a variety of temperatures that may range from −196 degrees C. to 37 degrees C. The distal end portion 18 of the lumen 10 is configured to receive a biological sample therein. In one non-limiting example, the particular embodiment illustrated in FIG. 5 may find application in the cryopreservation of a semen sample 58 containing millions of sperm cells, but may also be used for containing, preserving and/or storing a variety of biological samples.

FIGS. 1 and 4 illustrate another example of a container 4 which may find particular application in the vitrification of biological samples, including the vitrification of one or more embryos. As shown there, the closure member 40 includes a capping portion 42 and a sealing member 52 as described above, and preferably further includes a stem 60 extending from the sealing member 52. A trough or hook 62 is formed near the distal tip 64 of the stem 60 for holding and retaining a specimen, such as an embryo suspended in a droplet of vitrification media. The embryo may remain in the hook portion of the stem during vitrification and storage in the container 4.

The container 4 and the closure 40 that together make up cryocontainer 2 are preferably constructed of the same material so as to ensure the same thermal contraction properties of the respective materials including but not limited to polypropylene, polyethylene, polycarbonate and/or COC (cyclic olefin copolymer), although it is also contemplated that any material that is biocompatible with the particular biological sample and suitable for cryopreservation and/or vitrification may be used. Alternatively, the container 4 and closure 40 may be constructed of different materials having the same or substantially similar thermal and mechanical properties. Thus, as the container 4 (containing a biological sample and sealed with the closure member) is subjected to the extreme temperature changes and high cooling rates required for proper cryopreservation and/or vitrification, the sealing member 52 and internal lumen surface 14 maintain a tight and secure sealing engagement so as to isolate the sample receiving chamber 20 near the distal end portion 8 of the lumen (and any sample held therein) from the external environment while also preventing inadvertent leakage or seepage of gasses or liquids (including liquid nitrogen) into the sample chamber 20 of the lumen 10, even as the sealed container 2 is subjected to long term storage in liquid nitrogen. In other words, a "closed system" may be created and maintained for sealed storage of a sample in a variety of environments and temperature ranges, including during vitrification and storage in liquid nitrogen, without the need for providing additional or supplemental sealing measures to protect the samples during storage and/or to prevent liquid nitrogen from penetrating into the specimen-retaining chamber 20 of the container, such as shrink-tubing or heat-sealed sleeves over the container.

The above-described container may be used for cryopreservation and vitrification in accordance with the following exemplary methods. First, in one embodiment, a liquid sample may be placed directly into the container lumen. More particularly, any type of liquid sample, including but not limited to a semen sample 58 containing sperm cells, may be introduced into the distal sample-receiving portion 20 of the container lumen 10 as best shown in FIG. 5. The user may then secure the closure member 40 in place in the proximal open end 6, such as by screwing the capping portion 42 into the container. The corresponding engaging members on the container 4 and capping portion 42, such as the threads 44, 46, allow the closure member 40 to be securely held in place and also provide a signal to the user that the closure member 40 has been sufficiently screwed into the open end 6 when resistance is felt as the closure is being twisted into place.

A seal is created between the sealing member 52 and the internal lumen surface 14 of the container by the action of inserting and/or screwing the capping portion 42 into the vial 4. In other words, as the capping portion 42 is screwed into place, the deformable sealing member 52 is pushed distally into the lumen 10 such that the external surface of the sealing member 56 snugly abuts the correspondingly-shaped internal surface 14 of the lumen, providing a sealing engagement between the respective surfaces. As shown in FIGS. 4 and 5, the external surface 56 of the sealing member 52 provides a male taper that corresponds with the female taper provided by the internal surface 14 of the lumen, although, it is also contemplated that any correspondingly shaped surfaces may be provided to establish sealing engagement there between and thereby create a closed environment in the container lumen 10 for receiving and storing a biological sample. The biological sample held in the distal end 8 of the lumen 10 is thereby isolated from the external environment and is ready for cryopreservation and/or vitrification and storage. The container may be cooled by exposure to vapor-phase nitrogen, or more preferably, by submerging at least a portion of the container 4 into liquid nitrogen. For example, the container may be arranged into an organizer, rack, cane or the like and then placed into a chamber, tank, container or bath of liquid nitrogen in order to cool the biological sample within the container lumen to a suitable temperature. In a cryobanking facility, for example, a semen sample 58 may be cryopreserved in accordance with this exemplary method in order to maintain the viability of individual sperm cells which may be later thawed and used in various assisted reproduction applications.

In another exemplary method of use of a cryocontainer described herein, the container illustrated in FIG. 4 may find particular application in the vitrification of one or more biological samples, including, but not limited to the vitrification of an embryo. In one example of the method, a particular sample, such as an embryo suspended in a droplet of vitrification media, may be loaded or deposited by known and acceptable techniques onto the hook 62 located near the distal tip 64 of the stem 60, and then introduced into the container lumen for vitrification.

Depending on the particular procedure being performed, it may be desirable or necessary to prepare the container for receiving and vitrifying the specimen that has been loaded onto the stem tip, as described below. Preparation of the container may include, for example, pre-cooling the container 4 in a bath of liquid nitrogen. For example, the user may place the container into a rack such that at least the distal end 8 of the container is submerged in liquid nitrogen. The liquid nitrogen may flow into and between the radially outwardly extending projections 34 to fill the intermediate space 32 and surround the lumen wall. In this way, the lumen interior may be cooled by thermal transfer as external surface 14 of the lumen 10 is exposed to the liquid nitrogen flowing in the intermediate space 32. As a result, the internal lumen of the container becomes a region of cold air, having a temperature suitable for vitrifying a sample that is introduced into the sample-receiving portion 20 of the lumen 10. One or more containers may be "pre-cooled" in this way such that the containers are sufficiently prepared for receiving and vitrifying a sample, such as an embryo, introduced within the lumen.

With one or more containers 4 ready and waiting in a pre-cooled condition such that the internal lumen is at thermal equilibrium, the closure member 40, having an embryo (or other sample) retained on the tip of the stem 60 that extends from the container cap 42, can be inserted into the lumen 10. Once the distal tip 64 of the stem, holding an embryonic sample thereon, has been inserted into the lumen 10 and is properly positioned within the sample-receiving portion 20 at tapered distal end 8, the user may then secure the closure member 40 in place such as by screwing the capping portion 42 into the open end 6 of container in a manner similar to that already described above. The region of cold air within the lumen created by the liquid nitrogen (or other suitable cooling medium) surrounding the lumen wall provides the proper temperature and environment in the lumen, to vitrify the sample held on the stem tip without direct contact with the liquid nitrogen, achieving over 1,000 degrees C/min of cooling rate. Again, as previously described, the seal is created between the external surface 56 of the deformable sealing member 52 abutting the internal surface 14 of the container lumen by the action of inserting and/or screwing the capping portion 42 into the container, such that the sealing engagement between the respective surfaces provides an isolated chamber within the lumen, thus sealing the sample on the stem tip from the external environment. The vitrified sample is retained in this closed system within the container lumen which has been created by a leak-proof impermeable seal and is suitable for storage by known and acceptable methods, including storage in liquid nitrogen.

Throughout this specification, unless the context requires otherwise, the words "comprise" and "include" and variations such as "comprising" and "including" will be understood to imply the inclusion of an item or group of items, but not the exclusion of any other item or group items.

While various embodiments of the invention have been described, it will be apparent to those of ordinary skill in the art that many more embodiments and implementations are possible within the scope of the invention. Furthermore, although various indications have been given as to the scope of this invention, the invention is not limited to any one of these but may reside in two or more of these combined together. Accordingly, the invention is not to be restricted except in light of the attached claims and their equivalents.

The invention claimed is:

1. A sealable container comprising: a body comprising a proximal open end and a sealed distal end and a variable diameter lumen extending there between, the lumen having an external surface and an internal surface, the internal surface tapering generally radially inwardly from the proximal open end to the distal end and forming a sealing portion and a sample receiving portion, a closure configured for removable attachment to the body wherein the closure comprises a capping member adapted for engagement with the proximal open end and a deformable member having a tapered external surface configured for sealing engagement with the sealing portion of lumen internal surface, at least two projections extending radially outwardly from the external surface of the lumen, the projections comprising a radially outward-most surface extending between the proximal open end and the sealed distal end of the body, wherein the outward-most surface has a substantially constant diameter.

2. The container of claim 1 further comprising an intermediate space located between the external surface of the lumen and the outward-most surface of the projections.

3. The container of claim 1 wherein the container body comprises a single unitary piece of injection molded material.

4. The container of claim 3 wherein the material comprises polypropylene.

5. The container of claim 1 wherein the closure and the body comprise the same material.

6. The container of claim 1 wherein the closure and the body are constructed of a material that comprises the same or substantially similar thermal contraction properties.

7. The container of claim 1 wherein the proximal open end of the body comprises a threaded portion and wherein the closure comprises threads adapted for mating engagement with the threaded portion of the container body.

8. The container of claim 1 wherein the external surface of the deformable member comprises a male taper and the internal surface of the lumen comprises a female taper and wherein the male taper and female taper have corresponding taper angles such that an impermeable seal is established between the respective tapered surfaces.

9. The container of claim 1 wherein the diameter of the internal surface of the lumen varies from about 2 mm to about 7 mm.

10. The container of claim 1 wherein the diameter of the radially outwardly extending protrusions is approximately 12 mm.

11. The container of claim 1 wherein the closure further comprises a stem extending therefrom and wherein the stem comprises a proximal end configured for holding a biological sample.

12. The container of claim 11 wherein the stem comprises a proximal end that extends into the sample receiving portion of the internal lumen when the closure is secured to the container body.

13. A method for preparing a biological sample for cryogenic storage comprising: a. obtaining sealable container comprising: i. a body comprising a proximal open end and a sealed distal end and a variable diameter lumen extending there between, the lumen having an external surface and an internal surface, the internal surface tapering generally radially inwardly from the proximal open end to the distal end and forming a sealing portion and a sample receiving portion, ii. a closure configured for removable attachment to the body wherein the closure comprises a capping member adapted for engagement with the proximal open end and a deformable member having a tapered external surface configured for sealing engagement with the sealing portion of lumen internal surface, iii. at least two projections extending radially outwardly from the external surface of the lumen, the projections comprising a radially outward-most surface extending between the proximal open end and the sealed distal end of the body, wherein the outward-most surface has a substantially constant diameter; b. introducing a biological sample into the lumen of the container; c. attaching the closure to the container body.

14. The method of claim 13 wherein the biological sample is a suspension of cells, and the suspension is introduced into the distal end of the lumen.

15. The method of claim 13 wherein the biological sample is an embryo suspended in a cryoprotectant.

16. The method of claim 15 wherein the embryo is retained on a stem that extends from the capping member.

17. The method of claim 13 further comprising submerging at least a portion of the container into a volume of liquid nitrogen.

18. The method of claim 13 further comprising storing the container in a cryogenic freezing medium for a selected period of time.

19. A cryogenic storage method comprising: a. introducing a biological sample into the lumen of a container, the container comprising: i. a body comprising a proximal open end and a sealed distal end and a variable diameter lumen extending there between, the lumen having an external surface and an internal surface, the internal surface tapering generally radially inwardly from the proximal open end to the distal end and forming a sealing portion and a sample receiving portion, ii. a closure configured for removable attachment to the body wherein the closure comprises a capping member adapted for engagement with the proximal open end and a deformable member having a tapered external surface configured for sealing engagement with the sealing portion of lumen internal surface, iii. at least two projections extending radially outwardly from the external surface of the lumen, the projections comprising a radially outward-most surface extending between the proximal open end and the sealed distal end of the body, wherein the outward-most surface has a substantially constant diameter; b. exposing at least a portion of the container to a cryogenic freezing medium.

20. The method of claim 19 wherein the lumen of the container is pre-cooled to a temperature suitable for the vitrification of a biological sample prior to the step of introducing the biological sample into the lumen.

* * * * *